(12) United States Patent
Darling, IV

(10) Patent No.: US 12,082,812 B2
(45) Date of Patent: Sep. 10, 2024

(54) NON-INVASIVE WOUND CLOSURE DEVICE

(71) Applicant: DermaClip US, LLC, Houston, TX (US)

(72) Inventor: Charles M. Darling, IV, Houston, TX (US)

(73) Assignee: DermaClip US, LLC, Houston, TX (US)

( * ) Notice: Subject to any disclaimer, the term of this patent is extended or adjusted under 35 U.S.C. 154(b) by 0 days.

(21) Appl. No.: 18/482,322

(22) Filed: Oct. 6, 2023

(65) Prior Publication Data

US 2024/0115262 A1    Apr. 11, 2024

Related U.S. Application Data

(63) Continuation of application No. 16/855,759, filed on Apr. 22, 2020, now Pat. No. 11,779,339, which is a continuation-in-part of application No. 15/748,865, filed as application No. PCT/US2016/045103 on Aug. 2, 2016, now Pat. No. 10,631,862.

(60) Provisional application No. 62/201,170, filed on Aug. 5, 2015.

(51) Int. Cl.
*A61B 17/08* (2006.01)
*A61B 17/00* (2006.01)

(52) U.S. Cl.
CPC .. *A61B 17/085* (2013.01); *A61B 2017/00407* (2013.01); *A61B 2017/081* (2013.01)

(58) Field of Classification Search
CPC ........ A61B 17/085; A61B 2017/00407; A61B 2017/081
See application file for complete search history.

(56) References Cited

U.S. PATENT DOCUMENTS

| 6,022,351 A | 2/2000 | Bremer et al. |
| 2012/0203273 A1 | 8/2012 | Riskin et al. |
| 2014/0058444 A1 | 2/2014 | Fox |

OTHER PUBLICATIONS

Indian Office Action for IN App. No. 201817002581, Dated Jan. 13, 2021.
TW Office Action for App. No. 105125045, Dated Oct. 5, 2017.
PCT Search Report and Written Opinion for App. No. PCT/US2016/45103, Dated Oct. 24, 2016.
Chinese Office Action for App. No. 201680045752.7, Dated Sep. 2, 2020.

*Primary Examiner* — Phong Son H Dang
(74) *Attorney, Agent, or Firm* — Remenick PLLC

(57) ABSTRACT

Devices, tools, systems, kits and methods for closing a tissue opening non-invasively are presented. The devices include a tissue closure device that reliably induces eversion of tissue edges that define a tissue opening.

18 Claims, 5 Drawing Sheets

NON-INVASIVE WOUND CLOSURE DEVICE

REFERENCE TO RELATED APPLICATIONS

The present application is a Continuation of U.S. application Ser. No. 16/855,759, filed Apr. 22, 2020, which is a Continuation-In-Part of U.S. application Ser. No. 15/748,865, filed Jan. 30, 2018, which is a National Stage Application of Patent Cooperation Treaty Application No. PCT/US2016/45103, filed Aug. 2, 2016, which claims priority to Provisional U.S. Application No. 62/201,170, filed Aug. 5, 2015, all entitled "Non-Invasive Wound Closure Device," and all of which are incorporated in their entirety.

TECHNICAL FIELD

This invention is directed to tissue closure devices, tools, systems, kits, and methods for tissue repair and closure. In particular, the invention is directed to devices and methods that safely and securely close wounded tissue openings and permit and encourage healing to occur.

BACKGROUND ART

Closure of tissue openings, such as, for example, for surgical incisions and accidental lacerations or wounds, is critical both to minimize the risk of infection and to promote optimal healing of the wound or incision. Both of these outcomes require rapid wound closure and careful skin edge approximation. Closing a tissue opening or wound requires a mechanism for drawing both sides of a tissue opening together to promote healing and to reduce the formation of scar tissue.

Previous wound closure systems included various categories of materials passed through the skin, such as staples and sutures, substances that cover skin edges and hold them adjacent, such as glues, and adherent structures, such as strips. Suturing and stapling and tape procedures are invasive, which can traumatize and compromise the integrity of the tissue opening and the nutrient blood supply to the healing tissue edges. They cause pain, increase the possibility of infection, expose the surgeon, as well as the patient, to blood-borne disease, generally leave behind significant scars, and require a follow-up visit for suture or staple removal. Surgical glue is also used but is generally only adequate for small wounds or incisions where skin edges are not widely separated or under tension during closure. Tape procedures are generally ineffective for larger wounds and are not typically used for a variety of reasons in most surgical procedures.

Typical techniques of suturing to minimize the resulting blemish that occurs during the healing process require a threshold of dexterity that many care providers do not possess. This is particularly true in emergency situations, which often require immediate treatment to secure the tissue opening to allow for transport or until such time as proper surgery is possible. Suturing even by a skilled surgeon punctures and stresses tissue causing scarring. An easy to use, suture-less tissue opening closure system would be a great benefit in many situations.

Scientific principles show that good cosmetic outcomes in wound healing are largely determined by apposition and eversion created during wound closure. Eversion is critically important as expected scar formation includes myofibril contraction, which ultimately draws the scar slightly below the surrounding skin level. This is often seen in surgical scars, which have divots or slight depressions in the center. Eversion prevents or at least minimizes this phenomenon by starting with slightly raised skin that lays flat after the universal process of contraction, which occurs at about 2-3 weeks after injury. The medical community generally recommends skin edge eversion to promote the least noticeable scar. Unfortunately, skin edge eversion and apposition is difficult to achieve with simple stitches or glues. More complex stitches and devices that promote adequate eversion and apposition are time consuming to place and are used in less than one case in one hundred. Additionally, conventional tissue closure devices for tissue do not allow for the breathing and the egress of tissue fluids. Often, the durability of the applied tissue device is compromised by the impervious barrier to moisture and other substances beneath polymer components. This may lead to dislodgement of the tissue device.

SUMMARY OF THE EMBODIMENTS

The present invention overcomes the problems and disadvantages associated with current strategies and designs and provides new systems and methods of making devices for closing wounds.

One embodiment of the invention is directed to a non-invasive wound closure system. The system comprises a pair of identical closure components. Each closure component comprises an anchor comprised of a standoff assembly with an opening and an adhesive base below the standoff assembly, a ratcheting mechanism positioned within the opening, wherein a portion of the ratcheting mechanism is held in place by a connector tab on each side of the ratchet mechanism, which connector tab on each side is connected to the side of the housing in which the ratchet is located, and a pull tab extending from the anchor and adapted to mate with the opening of the standoff assembly of an opposing closure component. Each pull tab comprises teeth adapted to engage the ratcheting mechanism.

Preferably, in each closure component at least one tooth, when engaging the ratcheting mechanism is adapted to break the breakaway tab. In a preferred embodiment, the connector tab on each side of the ratcheting mechanism is designed to break away. Preferably, in each closure component a first breakaway connector is adapted to withstand more force than a second breakaway connector. In a preferred embodiment, in each closure component there are two teeth of different heights and a first, shorter tooth is adapted to break the second breakaway connector without breaking the first breakaway tab. Each ratcheting mechanism is preferably a flexible piece of material extending from an upper surface of the opening and one breakaway connector is positioned on either side of the ratcheting mechanism.

In a preferred embodiment, each closure component is a single piece of material. Preferably each closure component further comprises a tissue attachment base coupled to the anchor. Preferably each standoff assembly is comprised of a forward face from which the pull tab extends and a reward face, wherein the forward face is sloped rearward as it approaches the adhesive base. Preferably a closure component is positioned on opposite sides of a wound and the pull tab of each closure component engages the opening in the standoff assembly of the opposing closure component, as the pull tabs are pulled away from each other, the wound is closed such that the contact of the sloped forward faces of each standoff assembly cause eversion of tissue edges of the wound.

In a preferred embodiment, the adhesive base is porous. Preferably, the ratcheting mechanism is adapted to engage with the teeth of the opposing pull tab to allow the pull tab to enter the opening and prevents the pull tab from being withdrawn from the opening. The pair of closure components are preferably stored in a semi-engaged position prior to application to a patient. Preferably, multiple pairs of closure components are used to close a wound. Each anchor is preferably adapted to be attached to skin without piercing the skin.

Another embodiment of the invention is directed to a method of non-invasively closing a wound. The method comprises positioning a mated pair of identical closure components on either side of the wound and engaging the closure components by pulling the pull tabs apart, thereby forcing the sloped forward faces of each standoff assembly into contact and causing eversion of tissue edges of the wound. Each closure component comprises an anchor comprised of a standoff assembly with an opening and an adhesive base below the standoff assembly, a ratcheting mechanism positioned within the opening, wherein a portion of the ratcheting mechanism is held in place by at least one breakaway tab, a forward face from which the pull tab extends and a reward face, wherein the forward face is sloped rearward as it approaches the adhesive base, and a pull tab extending from the anchor and mated with the opening of the standoff assembly of an opposing closure component, wherein each pull tab comprises teeth adapted to engage the ratcheting mechanism.

Preferably, the method further comprises breaking each breakaway connector by engaging each ratcheting mechanism with the opposing pull tab. In a preferred embodiment, each ratcheting mechanism has two breakaway connectors. Preferably, each closure component a first breakaway connector is adapted to withstand more force than a second breakaway connector. In each closure component there are preferably two teeth of different heights and a first, shorter tooth is adapted to break the second breakaway connector without breaking the first breakaway connector. Preferably, each ratcheting mechanism is a flexible piece of material extending from an upper surface of the opening and one breakaway connector is positioned on either side of the ratcheting mechanism.

In a preferred embodiment, each closure component is a single piece of material. Preferably, each closure component further comprises a tissue attachment base coupled to the anchor. The adhesive base is preferably porous. Preferably, the ratcheting mechanism is adapted to engage with the teeth of the opposing pull tab to allow the pull tab to enter the opening and prevents the pull tab from being withdrawn from the opening. In a preferred embodiment, the method further comprises storing the pair of closure components in a semi-engaged position prior to application to a patient. In a preferred embodiment, the method further comprises positioning and engaging multiple pairs of closure components to close a wound. Preferably, the method further comprises affixing the closure components to skin of a patient without piercing the skin.

The invention is directed to devices, systems and methods for closing surgical incisions and non-surgical wounds that provide for improved wound care. In accordance with an embodiment of the invention, a tissue closure device for non-invasively closing a tissue opening includes an assembled pair of substantially identical closure components. Each component includes a tissue attachment base with an attachment mechanism on a first side thereof to affix the attachment base to the skin. A standoff assembly is mounted on a second side of the attachment base of each component. A toothed pull-tab, having first and second ends, is coupled to the attachment base of each component through the standoff assembly and defines a longitudinal axis. The standoff assembly has a forward face, to which the first end of the pull-tab is affixed, and an opposed rearward face, the forward face including a sloped portion that is sloped rearward as it approaches the attachment base. Each component further includes a female connective element, mounted on the second side of the attachment base, and which is built into the standoff assembly, that receives and engages the pull-tab from the other component and into which the pull-tab from the other component has been placed. Each pull-tab has a length sufficient to reach and be received by the female connective element of the other closure component. When the loaded assembled pair is affixed to the skin with each of the attachment bases disposed on an opposite side of the tissue opening, the device can be manipulated to adjust the spacing between the arms and causes the second ends of the pull-tabs to be pulled away from each other. This brings the sloped portions of the forward faces of the components into substantial contact with one another at a location of contact, causing each standoff assembly to pivot about the location of contact, inducing eversion of tissue edges that defined the opening.

In accordance with further embodiments of the invention, a female connective element of a tissue closure device may have a releasable tab-locking mechanism configured to releasably lock the pull-tab in position. The releasable tab locking mechanism may include a releasable finger having a tip that engages against such pull-tab. The finger may have an unreleased position wherein the tip engages against such pull-tab and a released position wherein the pull-tab can be freely moved, the finger being biased in the unreleased position. In various embodiments, a ratchet/piston locking mechanism may be provided that allows for precise closure and locking of the paired components. By depressing the piston, the locking mechanism is securely unlatched. The releasable tab-locking mechanism may be manipulated by hand, or may require a tool, for example, tweezers or a needle. More particularly, in various embodiments, the tab-locking mechanism may include a hollow recess. A tool, for example a needle, can be used to unlock the locking mechanism, for example by engaging the end of the needle into the hollow recess of the locking mechanism, applying force to the locking mechanism through the tool, and with that force unlocking the locking mechanism. The releasable tab-locking mechanism allows for drainage of wound edema and/or the treatment of infection, without removal and reapplication of the device. Such a feature can also be helpful when a wound needs to be temporarily left open to facilitate healing.

In accordance with further embodiments of the invention, the attachment base of a tissue closure device may be porous to allow for tissue breathing and the egress of tissue fluids. In various embodiments, the tissue closure device may have predefined holes placed on the attachment base that is seated on the tissue opening. Human tissues, unlike many other mammalian species, respire, produce oils and moisture. These physiologic processes result in premature dislodgement and migration of the device and thereby render the device ineffective. This is overcome by placement of a critical mass of openings to allow for evaporation and drainage of said fluids and gasses without effecting adhesive performance.

In accordance with further embodiments of the invention, the tissue closure device may be made of a biodegradable polymer. The attachment mechanism may include at least one of a hook and an adhesive. A strip of a plurality of tissue closure devices may be provided, wherein the tissue closure devices are held in spaced relationship to one another along at least one strip. For example, the tissue closure devices may be held in a parallel spaced relationship to one another along at least one strip.

Another embodiment of the invention is directed to a non-invasive wound closure system. The system comprises a pair of identical closure components, each closure component comprising an anchor comprised of a standoff assembly with an opening and an adhesive base below the standoff assembly, a ratcheting mechanism positioned within the opening, and a pull tab extending from the anchor and adapted to mate with the opening of the standoff assembly of an opposing closure component. Each opening having a gradually increasingly sloped inner surface and each pull tab comprises teeth adapted to engage the ratcheting mechanism.

Preferably, the gradually increasingly sloped inner surface is adapted to force at least one tooth up and into the standoff assembly to prevent the pull tab from being inadvertently withdrawn from the opening. In a preferred embodiment, each ratcheting mechanism has at least one breakaway connector. In each closure component, preferably a first breakaway connector is adapted to withstand more force than a second breakaway connector. Preferably, in each closure component there are at least two teeth, the are teeth of the same or different heights and a first tooth is adapted to break at least one of the breakaway connectors without breaking the other breakaway connector.

In a preferred embodiment, each ratcheting mechanism is a flexible piece of material extending from an upper surface of the opening and one breakaway connector is positioned on either side of the ratcheting mechanism. Preferably, each closure component is a single piece of material. The system preferably further comprises a tissue attachment base coupled to the anchor of each closure component. Preferably, each standoff assembly is comprised of a forward face from which the pull tab extends and a reward face, wherein the forward face is sloped rearward as it approaches the adhesive base. In a preferred embodiment, when a closure component is positioned on opposite sides of a wound and the pull tab of each closure component engages the opening in the standoff assembly of the opposing closure component, as the pull tabs are pulled away from each other, the wound is closed such that the contact of the sloped forward faces of each standoff assembly cause eversion of tissue edges of the wound.

The adhesive base is preferably porous. Preferably, the ratcheting mechanism is adapted to engage with the teeth of the opposing pull tab to allow the pull tab to enter the opening and prevents the pull tab from being withdrawn from the opening. In a preferred embodiment, the pair of closure components are stored in a semi-engaged position prior to application to a patient. Preferably, multiple pairs of closure components are used to close a wound. Each anchor is preferably adapted to be attached to skin without piercing the skin.

Another embodiment of the invention is directed to a method of non-invasively closing a wound. The method comprises the steps of positioning a mated pair of identical closure components on either side of the wound and engaging the closure components by pulling the pull tabs apart, thereby forcing the sloped forward faces of each standoff assembly into contact and causing eversion of tissue edges of the wound. Each closure component comprising: an anchor comprised of a standoff assembly with an opening and an adhesive base below the standoff assembly, a ratcheting mechanism positioned within the opening, a forward face from which the pull tab extends and a reward face, wherein the forward face is sloped rearward as it approaches the adhesive base, and a pull tab extending from the anchor and mated with the opening of the standoff assembly of an opposing closure component, wherein each pull tab comprises teeth adapted to engage the ratcheting mechanism. Each opening having a gradually increasingly sloped inner surface.

The method preferably further comprises securing the pull tab within the opening by forcing at least one tooth up and into the standoff assembly with the gradually increasingly sloped inner surface. Preferably, each ratcheting mechanism has at least one breakaway connector. In a preferred embodiment, in each closure component a first breakaway connector is adapted to withstand more force than a second breakaway connector. Preferably, in each closure component there are at least two teeth, the teeth are of the same or different heights and a first tooth is adapted to break at least one of the breakaway connectors without breaking the other breakaway connector. Preferably, each ratcheting mechanism is a flexible piece of material extending from an upper surface of the opening and one breakaway connector is positioned on either side of the ratcheting mechanism.

Each closure component is preferably a single piece of material. In a preferred embodiment, each closure component further comprises a tissue attachment base coupled to the anchor. The adhesive base is preferably porous. Preferably, the ratcheting mechanism is adapted to engage with the teeth of the opposing pull tab to allow the pull tab to enter the opening and prevents the pull tab from being withdrawn from the opening. The method preferably further comprises storing the pair of closure components in a semi-engaged position prior to application to a patient. The method preferably further comprises positioning and engaging multiple pairs of closure components to close a wound. The method preferably further comprises affixing the closure components to skin of a patient without piercing the skin.

Other embodiments and advantages of the invention are set forth in part in the description, which follows, and in part, may be obvious from this description, or may be learned from the practice of the invention.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1A:
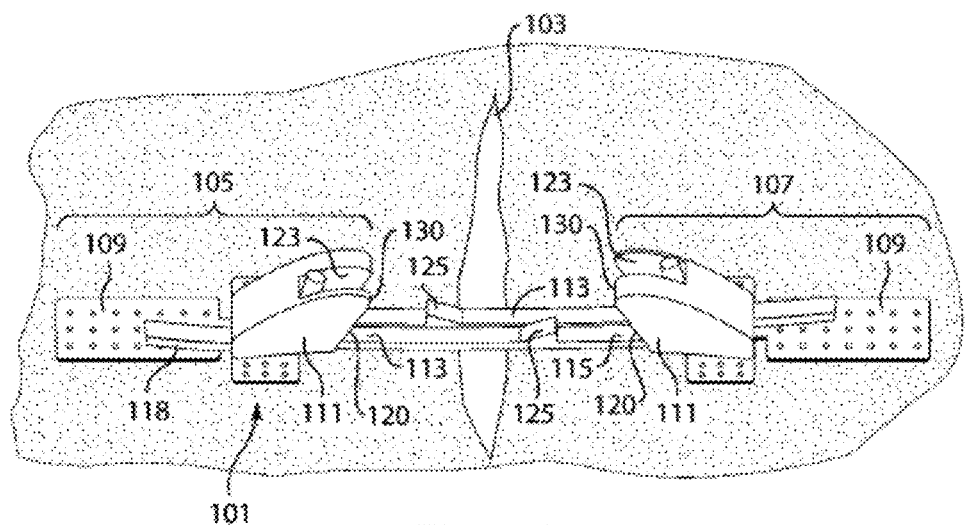
FIG. 1A shows an oblique view of a tissue closure device applied to a tissue opening prior to an operator effectuating tissue closure, in accordance with an embodiment of the invention.

Definitions. As used in this description and the accompanying claims, the following terms shall have the meanings indicated, unless the context otherwise requires:

A "tissue opening" refers to any surgical incision, accidental laceration or other form of injury. A tissue opening may be a wound in the skin, or to a tissue within a living or dead body, such as an organ. The tissue opening may be associated with any animal, including human and non-human animals. In some embodiments, the tissue opening may be associated with a mammal or a non-human mammal. A tissue opening may be of any shape or size.

"Apposition" refers to the proper alignment of skin edges to prevent gaps or mismatch.

"Eversion" is the turning outward of the edges of a wound or incision in order to bring the live dermis on the underside of the outer layer of the skin into contact.

In illustrative embodiments of the invention, devices, tools, systems, kits and methods for closing a tissue opening non-invasively are presented. The devices include a tissue closure device that reliably induces eversion of tissue edges that define a tissue opening. The devices may be used in combination with an applicator tool to provide easy and uniform apposition of the tissue closure devices across the tissue opening. Further embodiments may provide for releasable locking of the tissue closure devices, allowing for drainage of wound edema and/or treatment of infection, without removal and reapplication of the devices. Still further embodiments may allow for the passing of moisture or other substances that may collect under a tissue closure device. Details are discussed below.

An embodiment of the invention is directed to a device having two halves, each half composed of a polypropylene or other resin piece. The polypropylene piece is a unitary structure with the following elements along its continuance: an anchoring element; a living hinge connecting the anchoring element and the closure element; and the closure element. The entirety of the polypropylene piece has adhesive attached to it on its base side; the "base adhesive"; the top element of the adhesive sandwich is an adhesive attached to the top side of the anchoring element alone, stopping prior to the living hinge. In this manner an adhesive sandwich enclosing the anchoring element is created so as to securely bind the device to the skin. There is a pulling tab attached to the closure element of the polypropylene piece. This pulling tab is threaded through the closure element of the other polypropylene piece on the other half of the polypropylene piece so as to join the two halves together.

The base adhesive of each half of the device is placed on the skin with the outer edge of the closure element of the polypropylene piece attached to, and approximating, the edge of the incision or wound. In closure, the living hinge pivots so as to allow the closure device to pull the approximated edges of the wound held by each half of the joined device toward each other and then upward so as to cause eversion of the approximated edges of the skin upon closure. To effect closure, the pulling tabs attached to and part of the polypropylene piece are pulled away from each other so as to force closure of the device.

As to the anchoring element, holes have been put into the anchoring element so as to render it porous. The non-porous adhesive, combined with the porosity induced into the polypropylene, allows the wound to breath and exudate.

Figure 1B:
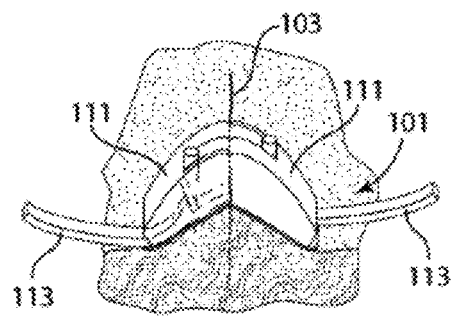
FIG. 1B shows an oblique view of the tissue closure device of FIG. 1A after the operator effectuates tissue closure.

FIG. 1A shows an oblique view of a tissue closure device 101 applied to a tissue opening 103 prior to an operator effectuating tissue closure, while FIG. 1B shows an oblique view of the tissue closure device of FIG. 1A after the operator effectuates tissue closure, in accordance with various embodiments of the invention. The tissue closing device 101 may be made of various materials, including, without limitation, plastic, metal, polypropylene, high-density polypropylene, and other polymers or thermoplastic materials, or combinations thereof. In various embodiments, the materials used for the tissue closure device 101 will be light, strong, and/or waterproof. It is possible that with some materials, the tissue closure device 101 may be cleaned and sterilized for reuse. The tissue closure device 101 may be applied under sterile or medically clean conditions depending on the type of wound and according to the best judgment of the healthcare provider. In some embodiments, the tissue closure device 101 (or one or more members thereof) includes an agent, such as for example a chemical, to detect and signal impending infection or treat the wound. Alternatively, in some embodiments, such an agent may be added to or above the closure during or after the procedure. In some embodiments the wound closure components may be made of bioabsorbable materials, such as a polysaccharide material. Bioabsorbable materials may advantageously be used to close a tissue opening within a living body, whereupon extra surgery is not needed for removal of the tissue closure device 101.

The tissue closure device 101 includes an assembled pair of substantially identical closure components 105 and 107. Each of the closure components 105 and 107 includes a tissue attachment base 109 with an attachment mechanism on a first side (e.g., the underside of the tissue attachment base 109). The attachment mechanism is used to affix the attachment base 109 to, without limitation, the skin or other tissue. The attachment mechanism may be an adhesive. The adhesive may be designed such that the user has some time to make minor placement adjustments before the adhesive adheres to the skin surface. This time can range from approximately ten seconds to approximately three minutes, and in a preferred embodiment is approximately one minute. The adhesive may be, without limitation, a pressure sensitive adhesive. In various embodiments, the attachment mechanism may include one or more hooks to affix the attachment base to the skin or other tissue.

A standoff assembly 111 is mounted on a second side of the attachment base 109 of each closure component 105 and 107. A pull-tab 113, having first and second ends 115 and 118, respectively, is coupled to the attachment base 109 through the standoff assembly 111 and defines a longitudinal axis. The standoff assembly 111 has a forward face 120, to which the first end 115 of the pull-tab 113 is affixed, and an opposed rearward face. The forward face 120 includes a sloped portion that is sloped rearward as it approaches the attachment base 109.

Each of the closure components 105 and 107 also include a female connective element 123 mounted on the second side of the attachment base 109 and built into the standoff assembly 111. The female connective element 123 receives and engages the pull-tab 113 from the other component. When the closure components 105 and 107 are engaged, the pull-tab 113 of each closure component 105 and 107 member passes through the female connective element 123 of the other member. The pull-tab 113 has teeth 125 rising from its upper surface. Upon entry of a pull-tab 113 into its associated female connective element 123, the female connective element 123 prevents teeth 125 passing through the female connective unit 123 from backing out. As described in further detail below, the female connective element 123 may include a releasable tab-locking mechanism.

As the pull-tabs 113 are pulled through female connective element 123 of the other closure component 105 and 107, the closure components 105 and 107 and hence the edges of the tissue opening to which the attachment base 109 is adhered to, move closer to each other. Further pulling brings the sloped portions of the forward faces 120 of the closure component components 106 and 107 into substantial contact with one another at a location of contact 130, whereupon each standoff assembly 111 pivots about the location of contact 130, as shown in FIG. 1B. When this occurs, respective portions of the undersurfaces of each tissue attachment base 109, which have adhesive covering and which are adhered to the skin or other tissue during use, are lifted, inducing eversion of the tissue edges that define the tissue opening. To facilitate wound edge eversion, the tissue closure device preferably has pull-tabs 113 in the lower one third of the height of each standoff assembly 111, and preferably has locations of contact 125 in the top one third of the height of each standoff assembly 111.

It is preferred that the tissue opening to be treated is smaller than the length of the pull-tabs. However, even for a tissue opening larger than the length of the pull-tabs, the members can be applied to both sides of the opening and manually brought together to allow the pull-tabs to engage with the respective openings on paired members. A further benefit of certain embodiments of the invention is that wounds can be closed over the course of multiple application steps. The person applying the tissue closure devices can choose to engage the members and close the tissue opening either partially or fully. Accordingly, the device preferably has at least one tooth to accomplish complete engagement of the device in the closed position but may have a total of two or more teeth to allow a partial closure or a series of partial closures reducing edge separation until full closure and edge eversion is accomplished by engaging the last tooth.

Figure 2:
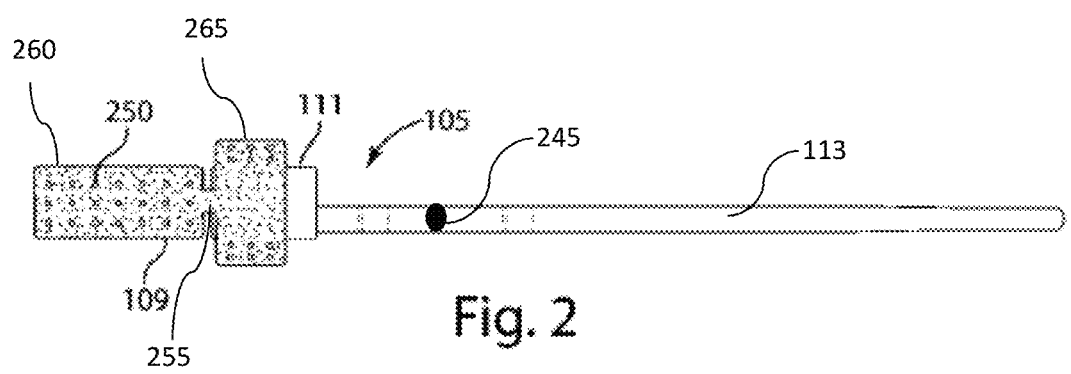
FIG. 2 shows a bottom view of a closure component, in accordance with an embodiment of the invention.
Figure 3:
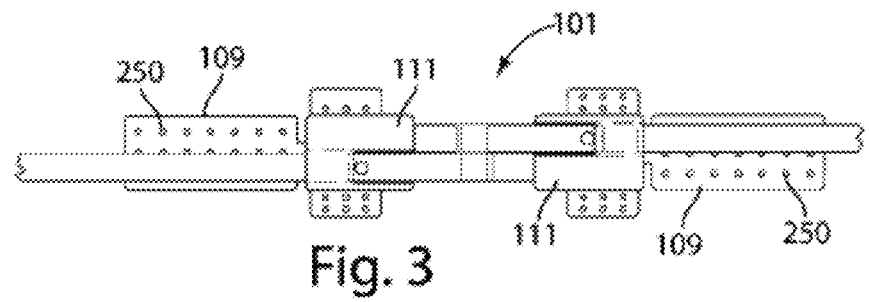
FIG. 3 shows a top view of an engaged tissue device, in accordance with an embodiment of the invention.

FIG. 2 shows a bottom view of closure component 105, while FIG. 3 shows a top view of the engaged tissue closure device 101, in accordance with various embodiments of the invention. The attachment base 109 of the closure devices 105 and 107 may be porous to allow for tissue breathing and the egress of tissue fluids. Human tissues, unlike many other mammalian species, respire, produce oils and moisture. These physiologic processes may result in premature dislodgement and migration of the device 101 and thereby render the device 101 ineffective. This may be overcome by making the attachment base 109 porous. For example, the attachment base 109 may include porous material, and/or a critical mass of one or more predefined holes 250, that allow for tissue breathing and the egress of tissue fluids and/or gasses without effecting the adhesive performance of the device 101. Attachment base 109 is preferably comprised of two portions connected by a linkage 255. Preferably, linkage 255 is a flexible portion of base 109 coupling the two portions of base 109.

Preferably, attachment base 109 has a first, narrower portion 260 that is positioned adjacent to standoff assembly 111 and a second, wider portion 265 to which standoff assembly 111 is coupled. Preferably, standoff assembly 111 is equal in width to narrower portion 260. Preferably, standoff assembly 111 is 50% the width of wider portion 265, 75% the width of wider portion 265, or equal in width to wider portion 265. Preferably, the greater portion standoff assembly 111 covers of wider portion 265 the greater the stability of device 101 upon application to a wound. Larger standoff assemblies 111 preferably reduce torsional forces experienced by smaller standoff assemblies 111. Preferably, pull-tab 113 is 30% the width of standoff assembly 111, 40% the width of standoff assembly 111, or 45% the width of standoff assembly 111.

In a preferred embodiment, pull-tab 113 has a breakaway portion 245. Breakaway portion 245 preferably allows the end of pull-tab 113 to be removed once device 101 is placed on a wound, thereby avoiding the need to cut off the end of pull-tab 113. For example, breakaway portion 245 may be a twist off portion, a hinge that breaks upon bending, a thinner portion of material that breaks once a certain amount of tension is applied, or another removal device. For example, breakaway portion 245 may be adapted to bear the tension necessary to close device 101 but will break once slightly more tension is applied. Preferably, breakaway portion 245 will break with minimal deformation. Preferably, breakaway portion 245 does not disrupt the adhesion of device 101 to the patient's skin or the positioning of the edges of the wound. In another embodiment, the end of pull-tab 113 may have adhesive that allows them to be affixed to the rest of device 101 and/or the patient's skin to keep the end secure.

The female connective element 123 of each closure device 105 and 107 may have a releasable tab-locking mechanism configured to releasably lock the pull-tab 113 in position. Such a locking mechanism may be unlocked by a tool, for example, tweezers or a needle, or in some embodiments a human finger, and the lock can subsequently be reengaged on the pull-tab to relock the pull-tab. The releasable tab-locking mechanism advantageously allows for drainage of wound edema and/or the treatment of infection, without removal and reapplication of the device. Such a feature can also be helpful when a tissue opening needs to be temporarily left open to facilitate healing.

Figure 4A:
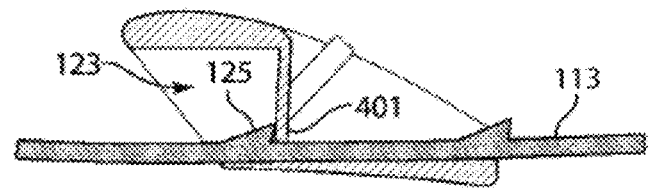
FIG. 4A shows a cross-section of a female connective element in an unreleased position, in accordance with an embodiment of the invention.
Figure 4B:
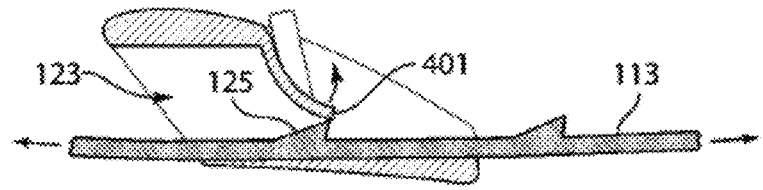
FIGS. 4B and 4C show cross-sections of the female connective element of FIG. 4A in released positions, wherein the pull-tab can be freely moved.
Figure 4C:
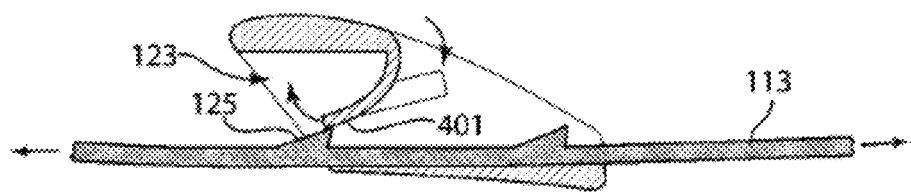

FIG. 4A shows a cross-section of a female connective element 123 in an unreleased position, in accordance with an embodiment of the invention. Illustratively, the releasable tab locking mechanism may include a releasable finger 401. The releasable finger 401 may be, for example, positioned in a recess, such that a tool is required to manipulate the finger 401. In other embodiments the finger 401 may protrude from the recess such that it can be manipulated without a special tool. The releasable finger 401 may have a tip that can engage against the teeth 125 the pull-tab 113. For example, in the unreleased position, the tip of the finger 401 may engage against a tooth 125 on the pull-tab, the finger 401 being biased in the unreleased position. By rotating the finger forward or backward, as shown in FIGS. 4B and 4C respectively, a released position is obtained wherein the pull-tab can be freely moved.

Figure 5:
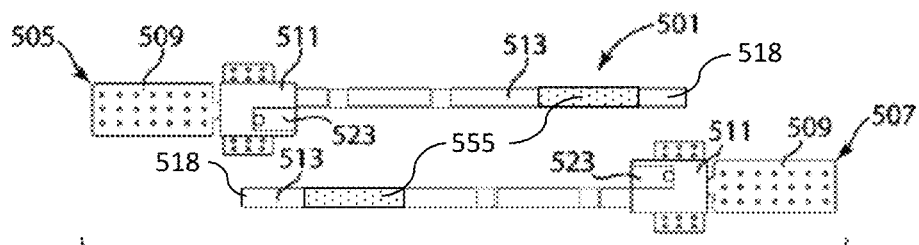
FIG. 5 shows a top view of a pair of closure devices of a tissue closure device in an unengaged position, in accordance with an embodiment of the invention.
Figure 6:
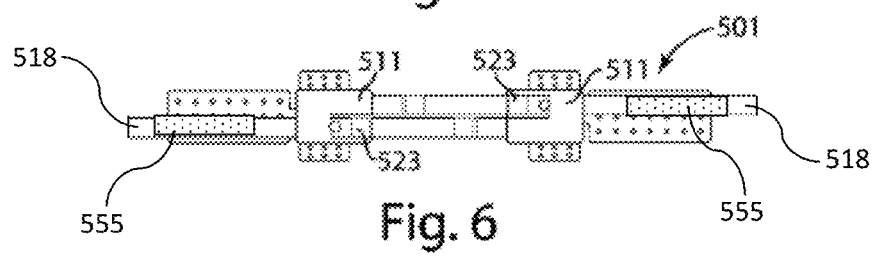
FIG. 6 shows a top view of the tissue closure device of FIG. 5 in an engaged position.
Figure 7:
FIG. 7 shows an oblique view of the tissue closure of FIG. 5 in an engaged position.

In illustrative embodiments of the invention, FIG. 5 shows a top view of a pair of closure devices 505 and 507 of a tissue closure device 501 in an unengaged position. FIG. 6 shows a top view of the tissue closure device 501 of FIG. 5 in an engaged position, and FIG. 7 shows an oblique view of the tissue closure device 501 of FIG. 5 in an engaged position. As shown in FIGS. 5-6, the second end 518 of each pull-tab 513 may have a gripping device 555. For example, gripping device can be raised dimples, knurling, a rough surface, a sticky surface, or another easily gripped portion. The tissue closure device 501 can be placed about the wound, so that, when the loaded assembled pair of closure devices 505 and 507 is affixed to the skin or other tissue, with each of the attachment bases 509 disposed on an opposite side of the tissue opening, the second ends 518 of the pull-tabs 513 can be pulled away from each other. This in turn, brings the sloped portions of the forward faces of the components into substantial contact with one another at a location of contact, with each standoff assembly 511 pivoting about the location of contact, so as to induce eversion of tissue edges that defined the opening.

Figure 8A:
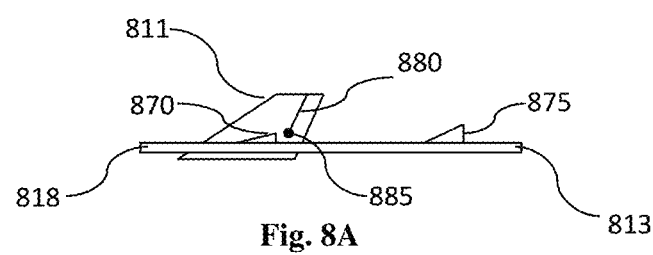
FIGS. 8A and 8B are cutaway side views of an embodiment of the device is a partially engaged position and a fully engaged position, respectively.
Figure 8B:
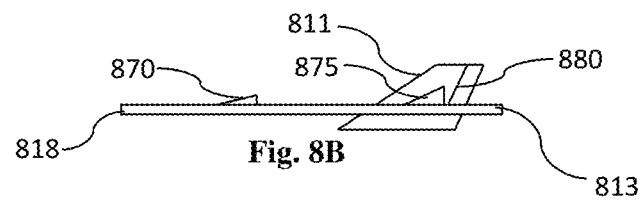

FIGS. 8A and 8B depicts another embodiment of a close up, cut away view of a pull-tab 813 inserted into standoff assembly 811. With FIG. 8A depicting pull-tab 813 inserted partially into standoff assembly 811 and FIG. 8B depicting pull-tab 813 inserted fully into standoff assembly 811. Preferably, each pull-tab 813 is comprised of at least two teeth, an anterior tooth 870 adjacent to end 818 and a posterior tooth 875 adjacent to standoff assembly 811. Preferably, anterior tooth 870 extends from pull-tab 813 a shorter distance than posterior tooth 875. During insertion of pull-tab 813 into standoff assembly 811 preferably anterior tooth 870 enters standoff assembly 811 before posterior tooth 875. The distance between anterior tooth 870 and posterior tooth 875 preferably determines the size of the wound device 801 can accommodate. Within standoff assembly 811 is preferably a ratchet 880. Ratchet 880 may hang freely within standoff assembly 811 or may be temporarily fixed within standoff assembly 811. In the embodiments where ratchet 880 is temporarily fixed within standoff assembly 811, preferably, ratchet 880 is held in place with a breakaway connector 885. In the preferred embodiment, anterior tooth 870 is tall enough to engage ratchet 880 without breaking breakaway connector 885 during insertion of pull-tab 813 into standoff assembly 811. Preferably, posterior tooth 875 is tall enough to break breakaway connector 885 during insertion of pull-tab 813 into standoff assembly 811. For example, anterior tooth 870 may inhibit pull-tab 813 from disengaging standoff assembly 811 (as shown in FIG. 8A), while posterior tooth 875 may prevent pull-tab 813 from disengaging standoff assembly 811 (as shown in FIG. 8B), since once breakaway connector 885 is broken, ratchet 880 may be able to further engage posterior tooth 875.

Figure 9:
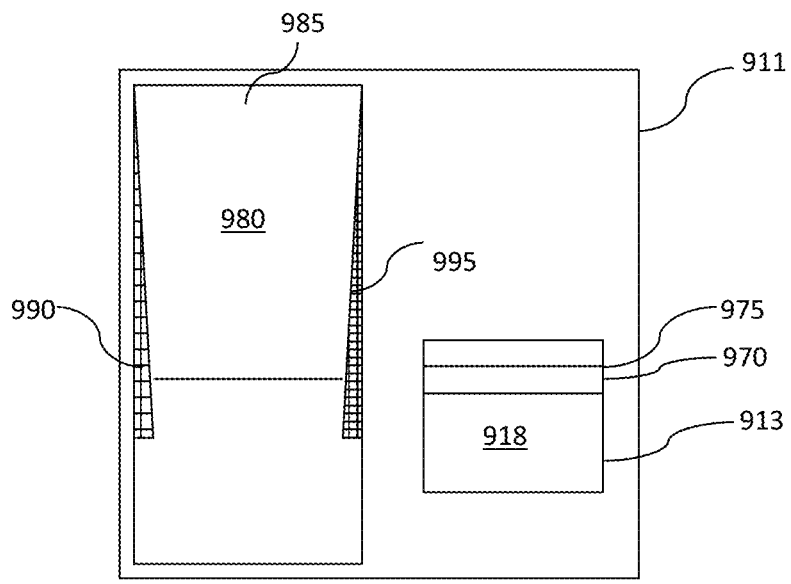
FIG. 9 is a front view of an embodiment of the standoff assembly.

FIG. 9 depicts a front view of another embodiment of a standoff assembly 911. Pull tab 913 preferably extends from standoff assembly 911 and is comprised of two teeth, an anterior tooth 970 adjacent to end 918 and a taller posterior tooth 975 adjacent to standoff assembly 911. Standoff assembly 911 further comprises a ratchet 980. Preferably, ratchet 980 is held into standoff assembly 911 along three edges. The upper edge 985 is preferably a fixed edge designed to maintain the connection between ratchet 980 and standoff assembly 911. The outer edge 990 is preferably a breakaway edge designed to allow ratchet 980 to move within standoff assembly 911 during insertion of pull tab 913. The inner edge 995 is preferably a second breakaway edge designed to allow ratchet 980 to move within standoff assembly 911 during insertion of pull tab 913. Outer edge 990 preferably requires less force to break than inner edge 995 such that as pull tab 913 is inserted into standoff assembly 911, anterior tooth 970 causes outer edge 990 to break but does not cause inner edge 995 to break. As posterior tooth 975 enters standoff assembly 911, inner edge 995 may break, may partially break, or may maintain the connection between ratchet 980 and standoff assembly 911. Preferably upper edge 985 does not break or weaken. While FIG. 9 depicts the weaker breakaway edge as the outer edge and the stronger breakaway edge as the inner edge, the edges can be reversed. A force of less than 15 N, less than 12 N, or less than 9 N is preferable to insert pull tab 913 into opposing standoff assembly 911. A force of more than 9 N, more than 12 N, more than 15 N, or more than 18 N is preferably to separate pull tab 913 from opposing standoff assembly 911. Preferably edges 990 and 995 reduce fatigue of upper edge 985 during insertion of pull tab 913.

The tissue closure device may be manufactured and provided to an operator in the engaged position, such that the second end already protrudes from the female connective element of the other closure component. Alternatively, the tissue closure device may be provided to an operator in the unengaged position, with the second end of each pull tab being dimensioned and/or having enough flexibility so as be capable of being passed through the female connective element of the other closure component.

Embodiments of the invention may be applied as follows. Assembly of the pairs of closure components that make up the closure device may be done prior to packaging and before the user receives the devices. Assembly may be done by pushing the pull-tabs of each closure component through the female connective element of its corresponding closure component, to initiate alignment and engage the paired closure devices. Adhesive backing may be applied to the tissue attachment base of each closure device, and an adhesive strip may be applied across the paired closure device to maintain proper alignment. The closure device may be loaded onto the applicator tool. Alternatively, the user may engage the pair(s) of closure components and/or load the closure device onto the applicator tool.

To apply the assembled closure devices to the tissue opening, the user may remove the adhesive backing from one closure component of the tissue closing device, or, in the case of multiple sets of paired closure components, from all closure components on one side of the engaged sets. The user may then place the closure component(s) with the adhesive backing removed on cleansed and dry skin so that their forward face(s) are abutting one edge of the tissue opening. The user then slowly brings the paired closure components together, one closure component of each pair attached to the skin on one side of the wound and the other closure component each pair not yet attached to the skin. The user continues to bring the paired connections together until the second component of each paired component is placed abutting an opposite skin edge. The user then removes the adhesive backing from the second component(s) and places the second component(s) near the wound edge. The adhesive may be selected such that the user has some time to make minor placement adjustments before the adhesive adheres to the skin surface. This time can range from approximately ten seconds to approximately three minutes, and in a preferred embodiment is approximately one minute. After this time elapses, the user gently brings the edges of the tissue opening wound edges toward each other. The user can, if desired, unlock the closure component(s) by manipulating the tab-locking mechanism.

Depending on the type of adhesive used, the closure device will naturally exfoliate within a period of at least approximately seven to ten days for longer duration closures. For other closures, the time may be shorter or longer. Alternatively, a user can apply a solvent to the adhesive for more immediate removal. If desired, the paired closure components can be loosened a variable distance, for example from approximately 1 mm to approximately 10 mm to allow for drainage of fluids and making the window a period of up to 14 days. The paired closure components can later tightened to re-close the tissue opening.

Figure 10:
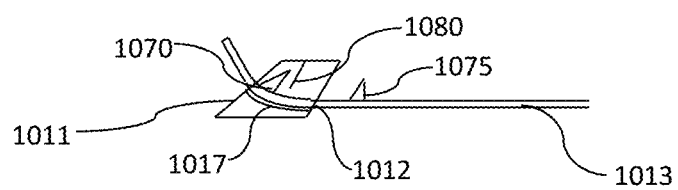
FIG. 10 depicts a cut away view of an embodiment with a gradually sloping internal surface.

FIG. 10 depicts another embodiment of a wound closure device. Preferably, the wound closure device has two halves each with a standoff assembly 1011, a pull tab 1013, and an attachment base or anchor. FIG. 10 shows the standoff assembly 1011 of one half of the wound closure device with the pull tab 1013 of the second half of the wound closure device inserted therein. The wound closure device preferably has a "ski ramp" or gradually increasing sloped inner surface 1017, which changes the angle of the tooth 1070 as the tooth comes into contact with the breakaway connector 1080. The change in the angle of the tooth 1070 forces the tooth up and into the locking device 1011 so that the ratcheting mechanism does not skip over the tooth and further secures pull tab 1013 into the opening of standoff assembly 1011 to enhance the lock of the pull tab 1013 into standoff assembly 1011 and to prevent the inadvertent removal of pull tab 1013 from standoff assembly 1011. Preferably, the halves are identical and preform in the same manner, however in other embodiments, only one half may have the sloped inner surface 1017.

Figure 11:
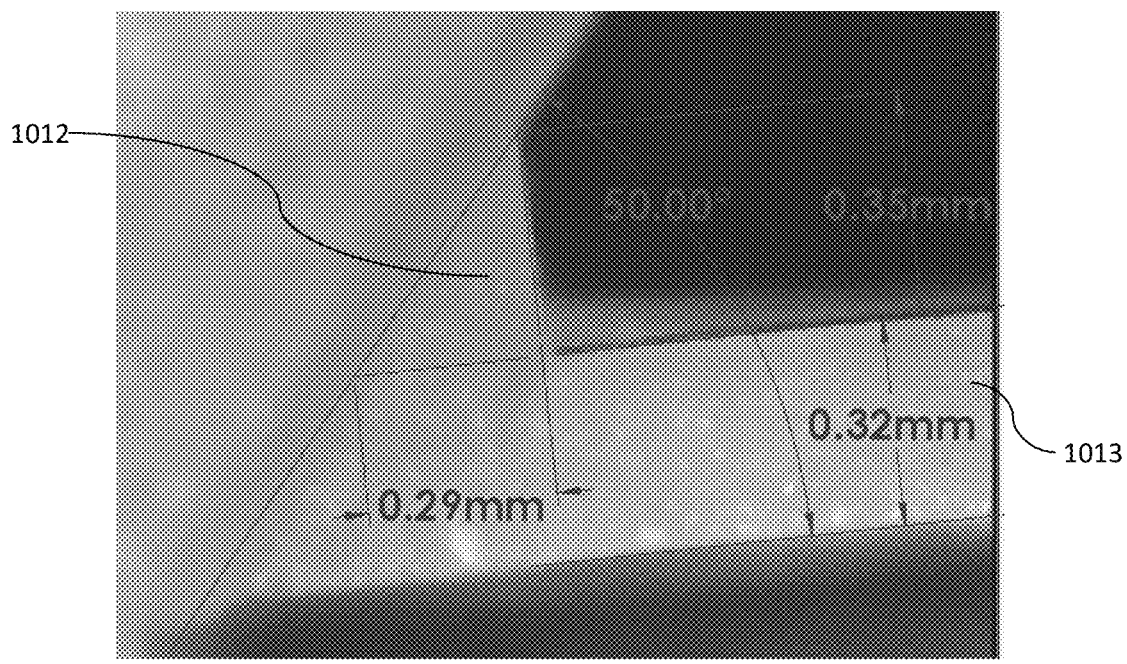
FIG. 11 depicts a close-up view of a chamfered opening.

Standoff assembly 1011 preferably also has a chamfered reinforcement 1012 (see FIG. 11) to reinforce the connection between the standoff assembly 1011 and the pull tab 1013. Preferably, chamfered reinforcement 1012 helps to prevent the accidental breakage of pull tab 1013 when the necessary force is applied to closure the wound closure device. Preferably, the material of the wound closure device is flexible enough to allow pull tab 1013 to bend to an acute angel (i.e. up to 90°) without breaking.

Other embodiments and uses of the invention will be apparent to those skilled in the art from consideration of the specification and practice of the invention disclosed herein. All references cited herein, including all publications, U.S. and foreign patents and patent applications, including U.S. application Ser. No. 11/217,127 and International Application No. PCT/US05/30890, both filed Aug. 31, 2005 and U.S. application Ser. No. 12/059,485 and International Application No. PCT/US09/38188, both filed Mar. 31, 2008, are specifically and entirely incorporated herein by reference in their entirety.

Although various exemplary embodiments of the invention have been disclosed, it should be apparent to those skilled in the art that various changes and modifications can be made that will achieve some of the advantages of the invention without departing from the true scope of the invention. For example, elements from one embodiment may be used in another embodiment. These and other obvious modifications are intended to be covered by the appended claims.

The invention claimed is:

1. A non-invasive wound closure system, comprising:
   a pair of identical closure components, each closure component comprising:
   a standoff assembly with an opening;
   an adhesive base below the standoff assembly; an adhesive anchor coupled to the adhesive base with a flexible hinge; and
   a pull tab extending from the anchor and adapted to mate with the opening of the standoff assembly of an opposing closure component;
   wherein a width of the adhesive base is equal to a width of the standoff assembly.

2. The non-invasive wound closure system of claim 1, further comprising at least one tooth coupled to the pull tab and adapted to engage the opening of the opposing closure component.

3. The non-invasive wound closure system of claim 1, wherein the adhesive base is porous.

4. The non-invasive wound closure system of claim 1, wherein the adhesive anchor is porous.

5. The non-invasive wound closure system of claim 1, wherein each closure component is a single piece of material.

6. The non-invasive wound closure system of claim 1, wherein each standoff assembly is comprised of a forward face from which the pull tab extends and a reward face, wherein the forward face is sloped rearward as it approaches the adhesive base.

7. The non-invasive wound closure system of claim 6, wherein, when a closure component is positioned on opposite sides of a wound and the pull tab of each closure component engages the opening in the standoff assembly of the opposing closure component, as the pull tabs are pulled away from each other, the wound is closed such that the contact of the sloped forward faces of each standoff assembly cause eversion of tissue edges of the wound.

8. The non-invasive wound closure system of claim 1, wherein the pair of closure components are stored in a semi-engaged position prior to application to a patient.

9. The non-invasive wound closure system of claim 1, wherein multiple pairs of closure components are used to close a wound.

10. The non-invasive wound closure system of claim 1, wherein each closure component is adapted to be attached to skin without piercing the skin.

11. A method of non-invasively closing a wound:
   positioning a mated pair of identical closure components on either side of the wound, each closure component comprising:
   a standoff assembly with an opening;
   an adhesive base positioned below the standoff assembly an adhesive anchor coupled to the adhesive base with a flexible hinge;
   the standoff assembly having a forward face from which a pull tab extends and a reward face, wherein the forward face is sloped rearward as it approaches the adhesive base; and
   wherein the pull tab is adapted to mate with the opening of the standoff assembly of an opposing closure component; and
   engaging the closure components by pulling the pull tabs apart, thereby forcing the sloped forward faces of each standoff assembly into contact and causing eversion of tissue edges of the wound.

12. The method of claim 11, wherein each pull tab has at least one tooth adapted to engage the opening of the opposing closure component.

13. The method of claim 11, wherein the adhesive base is porous.

14. The method of claim 11, wherein the adhesive anchor is porous.

15. The method of claim 11, wherein each closure component is a single piece of material.

16. The method of claim 11, further comprising storing the pair of closure components in a semi-engaged position prior to application to a patient.

17. The method of claim 11, further comprising positioning and engaging multiple pairs of closure components to close a wound.

18. The method of claim 11, further comprising affixing the closure components to skin of a patient without piercing the skin.

* * * * *